United States Patent
Lechner

(10) Patent No.: US 7,922,689 B2
(45) Date of Patent: Apr. 12, 2011

(54) DEVICE AND METHOD FOR LOCATING ANATOMICAL CAVITY IN A BODY

(76) Inventor: Timotheus Joan Marie Lechner, Drunen (NL)

(*) Notice: Subject to any disclaimer, the term of this patent is extended or adjusted under 35 U.S.C. 154(b) by 1494 days.

(21) Appl. No.: 10/481,527

(22) PCT Filed: Jun. 20, 2002

(86) PCT No.: PCT/NL02/00405
§ 371 (c)(1),
(2), (4) Date: Jun. 7, 2004

(87) PCT Pub. No.: WO03/000146
PCT Pub. Date: Jan. 3, 2003

(65) Prior Publication Data
US 2004/0215080 A1    Oct. 28, 2004

(30) Foreign Application Priority Data
Jun. 20, 2001 (NL) .................................... 1018334

(51) Int. Cl.
*A61M 31/00* (2006.01)
(52) U.S. Cl. .............. 604/66; 604/67; 606/191; 417/4
(58) Field of Classification Search .............. 604/6.11, 604/9, 65, 67, 123, 146, 188, 193, 194, 195, 604/196, 93.01; 417/4, 6, 14, 19, 25, 31, 417/38, 44.2, 44.3, 112, 115, 120, 142; 606/191
See application file for complete search history.

(56) References Cited

U.S. PATENT DOCUMENTS

| 3,867,934 A * | 2/1975 | Ollivier ................... 128/202.22 |
| 4,356,826 A | 11/1982 | Kubota |
| 5,269,762 A | 12/1993 | Armbruster et al. |
| 5,295,967 A | 3/1994 | Rondelet et al. |
| 5,520,650 A | 5/1996 | Zadini et al. |

(Continued)

FOREIGN PATENT DOCUMENTS

EP    0 303 824    2/1989

(Continued)

OTHER PUBLICATIONS

Hungarian Novelty Report, Application No. P 04 00176.

*Primary Examiner* — Brian Casler
*Assistant Examiner* — Amanda Lauritzen
(74) *Attorney, Agent, or Firm* — Hoffmann & Baron, LLP

(57) ABSTRACT

A device (1) is designed for locating a region which is situated in a body (10). The device has a fluid-filled reservoir (30) which is closed off in a sealed manner by a displaceable plunger (32) and is connected to a hollow puncture needle (20). To measure the pressure prevailing in the fluid, the device has a pressure gauge (40). A signal converter (50) is used to convert a continuous pressure-measurement signal provided by the pressure gauge (40) into a form which is suitable for further processing. A synthesizer (60) is designed to process the converted pressure-measurement signal into a continuous sound signal which is representative of the pressure. If, during a displacement of the puncture needle (20), a needle point (21) reaches the anatomical cavity (15), the result is a readily perceptible change in the sound signal. The device records the pressure-measurement signal over the course of time.

19 Claims, 2 Drawing Sheets

U.S. PATENT DOCUMENTS

| | | | |
|---|---|---|---|
| 5,681,285 A | 10/1997 | Ford et al. | |
| 5,690,618 A | 11/1997 | Smith et al. | |
| 5,954,701 A | 9/1999 | Matalon | |
| 6,022,337 A | 2/2000 | Herbst et al. | |
| 6,200,289 B1 | 3/2001 | Hochman et al. | |
| 6,569,147 B1 * | 5/2003 | Evans et al. | 604/509 |
| 6,705,990 B1 * | 3/2004 | Gallant et al. | 600/300 |
| 7,022,072 B2 * | 4/2006 | Fox et al. | 600/365 |
| 2002/0143294 A1 * | 10/2002 | Duchon et al. | 604/131 |
| 2003/0014006 A1 | 1/2003 | Alexandre et al. | |

FOREIGN PATENT DOCUMENTS

| | | |
|---|---|---|
| EP | 0 538 259 | 4/1993 |
| FR | 2 628 625 | 9/1989 |
| HU | P8806113 | 10/1990 |
| HU | P0204296 | 3/2003 |
| JP | A 5 042218 | 2/1993 |
| JP | A 6 007440 | 1/1994 |
| JP | A 6 142114 | 5/1994 |
| WO | WO 97/25081 | 7/1997 |

* cited by examiner

DEVICE AND METHOD FOR LOCATING ANATOMICAL CAVITY IN A BODY

CROSS-REFERENCE TO RELATED APPLICATIONS

This application is the national stage filing under 35 U.S.C.§371 of PCT/NL02/00405, filed Jun. 20, 2002, which claims priority to NL 1018334, filed Jun. 20, 2001, which is incorporated herein by reference.

FIELD OF THE INVENTION

The present invention relates to a device and a method for locating an anatomical cavity in a body.

BACKGROUND OF THE INVENTION

Locating an anatomical cavity in a body, for example the body of a patient, is important, inter alia, for anaesthetics, in which it is often necessary for substances which have an anaesthetic action to be introduced into the anatomical cavity, such as for example the epidural cavity which is located in the vicinity of the spinal cord. To locate the anatomical cavity, it is generally known to use a hollow needle and a reservoir filled with an isotonic liquid or with a gas mixture, often an injection syringe with a displaceable plunger. In this case, the hollow needle is introduced into a patient's body, in the vicinity of the location where the cavity which is to be located is situated. The injection syringe is positioned at the free end of the needle, and the liquid or gas mixture can be injected from the injection syringe through the needle and can reach the body of the patient. The person who is handling the injection syringe with the needle, for example a physician, uses one hand to introduce the needle further into the body and uses the thumb of the other hand to exert pressure on the plunger of the injection syringe. The liquid will seek to flow out of the injection syringe via the open end of the needle, but in the process will be subject to a resistance from the tissue in which the point of the needle is situated. As a result, a certain force will have to be exerted on the plunger, and a pressure will be produced in the liquid. When the point of the needle reaches the anatomical cavity, the liquid flowing out of the needle is no longer subject to any resistance from surrounding tissue, and the pressure in the liquid drops. The person who is handling the assembly can feel this in the hand which he is using to operate the injection syringe. When the epidural cavity has been reached, a catheter is often introduced via the needle into the epidural cavity, so that, for example, an anaesthetic substance can be administered.

When the epidural cavity is being located, it is highly important that the point of the needle should not pass beyond this cavity, since there is then a risk of the spinal cavity or spinal cord behind it being affected, which may have particularly adverse results for the patient. Therefore, all kinds of methods and devices have been developed which make it easier to locate an anatomical cavity and reduce the risk of the point of the needle being introduced too far.

An example of a method and device of this type is known, inter alia from EP 0 538 259.

The known device comprises a hollow needle, a fluid-filled reservoir which is in communication with the needle, pump means for pressurizing the fluid, measuring means for creating a pressure-measurement signal which is related to the pressure prevailing in the fluid, signal-conversion means for converting the pressure-measurement signal created by the measuring means into a form which is suitable for further processing, and reproduction means for emitting an acoustic signal which is related to the pressure-measurement signal which has been converted by the signal-conversion means.

The needle of the known device is intended to be introduced into a body and is connected to the reservoir in the form of an injection syringe. The injection syringe contains a fluid in the form of an isotonic liquid. The needle and the injection syringe are in communication with one another via a T-shaped connector. The pressure-measuring means, which are used to detect and measure the pressure prevailing in the liquid in the injection syringe, are also connected to this T-shaped connector. The known device also comprises a processor for processing a pressure-measurement signal created by the pressure-measuring means, in order that the rate of pressure variation can always be determined, which pressure variation is primarily the consequence of the movement of the needle in the body. The pressure data provided by the processor and the pressure-measuring means are continuously compared with margins stored in the processor.

When the known device is being used, the starting point is a situation in which the point of the needle is already situated in the vicinity of the cavity which is to be located. The needle, the injection syringe and the pressure-measuring means are connected to one another by changing the position of a switch. In the injection syringe there is a plunger which functions as a pump means for displacing the liquid through the needle and thus produces pressure in the liquid. The pressure which is shown on the screen when there is no pressure being exerted on the plunger of the injection syringe is calibrated to zero. Then, the person who is handling the injection syringe and the needle brings the pressure in the liquid in the injection syringe to a defined level by exerting pressure on the plunger. During this process, he can read the level of the pressure from the screen at any time. When the liquid in the injection syringe has been brought to the required pressure, the person who is handling the device can move the needle towards the cavity in the body while using the pressure data displayed on the screen to carefully maintain a pressure on the plunger. In the process, the pressure in the liquid will vary. When the level of the pressure variation exceeds a minimum level stored in the processor and/or the pressure variation rate over a defined time period is within minimum margins stored in the processor, the warning means are activated and emit a first, acoustic warning signal via acoustic reproduction means. If the pressure can be restored by slightly displacing the plunger, without further displacement of the needle, the first acoustic warning signal will stop. On the other hand, if a more abrupt pressure variation occurs and the pressure cannot be restored by displacing the plunger, the warning means emit a second, acoustic warning signal, which clearly differs from the first warning signal. From the second warning signal, the person who is handling the device can infer that the point of the needle has reached the anatomical cavity and that he must stop moving the needle.

A drawback of the device and method which are known from EP 0 538 259 is that the acoustic warning signals are emitted on the basis of an interpretation of the pressure data by the processor. Although the person who is handling the device can see the instantaneous pressure on the screen and can also feel this information through the plunger, he will quickly become inclined to depend only upon his hearing and trust the acoustic warning signals. However, in practice this has not proven satisfactory, and consequently the person who is handling the device will also look at the screen, so that he loses sight of the needle.

OBJECTS OF THE INVENTION

It is an object of the present invention to provide an improved device for locating an anatomical cavity in which the above drawback is eliminated or at least reduced.

SUMMARY OF THE INVENTION

According to the present invention, the above object is achieved by providing a device for locating an anatomical cavity comprising a hollow needle and a reservoir which is in communication therewith and is filled with a fluid. The reservoir is also connected to pump means for pressurizing the fluid. Furthermore, measuring means are provided for creating a pressure-measurement signal which is related to the pressure prevailing in the fluid, and signal-conversion means are provided for converting the pressure-measurement signal which has been created by the measurement means into a form which is suitable for further processing. Acoustic reproduction means are also provided, which are designed to emit an acoustic signal which is representative of the pressure prevailing in the fluid.

In the device according to the invention, the pressure is made continuously available to the person who is handling the device and to any onlookers who may be present during the introduction of the needle into the body by means of the acoustic signal, which is representative of the prevailing pressure and therefore of the pressure signal. The person who is handling the device can therefore use his hearing to obtain instantaneous pressure data continuously, which data is directly representative of the pressure in the needle which is coupled to the reservoir. Consequently, the person who is handling the device can continuously direct his eyes at the needle and does not have to work on the basis of visual information and/or tactile information. A particular advantage is that the interpretation of the measured pressure is the responsibility of the person who is handling the device, rather than of a processor, and therefore it is possible to draw an interpretation with regard to intra-individual pressure variations for each case.

A further drawback of the device and method which are known from EP 0 538 259 relates to the risk of the point of the needle being introduced too far. Although the known device reduces this risk, since the feeling of the person who is handling the device is assisted by the warning signals, the risk of the needle shooting through (too far) when the anatomical cavity is reached as a result of one hand being used to exert pressure on the needle and the other hand being used to exert pressure on the plunger of the injection syringe is still present. Since moving the needle requires a relatively large amount of force, this risk is by no means negligible.

This drawback is at least partially overcome by an important preferred embodiment of the device according to the present invention, which is provided with automatic pump means and in particular is provided with automatic pump means which are designed to continuously deliver the fluid.

When using the device according to the invention, the person who is handling the device continuously receives the instantaneous pressure data on the basis of his hearing, and therefore there is no need to feel the pressure in the fluid. The use of automatic pump means has the major advantage that the person who is handling the device can use both hands to move the point of the needle towards the anatomical cavity. When both hands are being used, the person who is handling the device is able to introduce the needle in a more controlled way than if only one hand is used for this purpose. Moreover, he does not now have to exert any force in order to generate the pressure, but rather only has to exert force on the needle.

In a further preferred embodiment of the device according to the invention, the pump means comprise a displaceable plunger, and the pump means are provided with a drive unit which is designed to displace the plunger in the reservoir, preferably at a constant rate.

The fact that the drive unit displaces the plunger, preferably at a constant rate, means that the force which is exerted on the plunger by the automatic pump means will always have to vary, since the point of the needle is constantly moving through different types of tissue as it is being introduced. In the case of a relatively firm tissue, the fluid which emerges from the needle will be subject to more resistance from the tissue than in the case of a soft tissue. When the point of the needle reaches the anatomical cavity, the fluid will flow into the anatomical cavity virtually without resistance, and therefore scarcely any force has to be exerted on the plunger. This consequently results in a considerable drop in the pressure of the fluid.

The risk of the point of the needle being introduced too far is considerably reduced compared to the device which is known from EP 0 538 259.

The device according to the invention is eminently suitable for use for training purposes, in particular for training medical personnel. An instructor can easily monitor the actions of a student or trainee and provide suitable instructions, since he can always hear information about the pressure state at the point of the needle. If the preferred embodiment with the drive means is being used, it has the additional advantage that the student or trainee only has to concentrate on the movement of the needle and can use both hands to do this.

The present invention also relates to a measuring and signalling device which is intended in particular to be used in the device for locating an anatomical cavity, and to a method for measuring the pressure in a fluid at the location of the point of a hollow needle which is situated in a body for the benefit of an observer.

BRIEF DESCRIPTION OF THE DRAWINGS

These and other aspects, characteristics and advantages of the present invention will be explained in more detail by means of the following description of two preferred embodiments of a locating device according to the invention with reference to the drawing, in which identical reference numerals denote identical components, and in which.

DETAILED DESCRIPTION OF THE INVENTION

Figure 1:
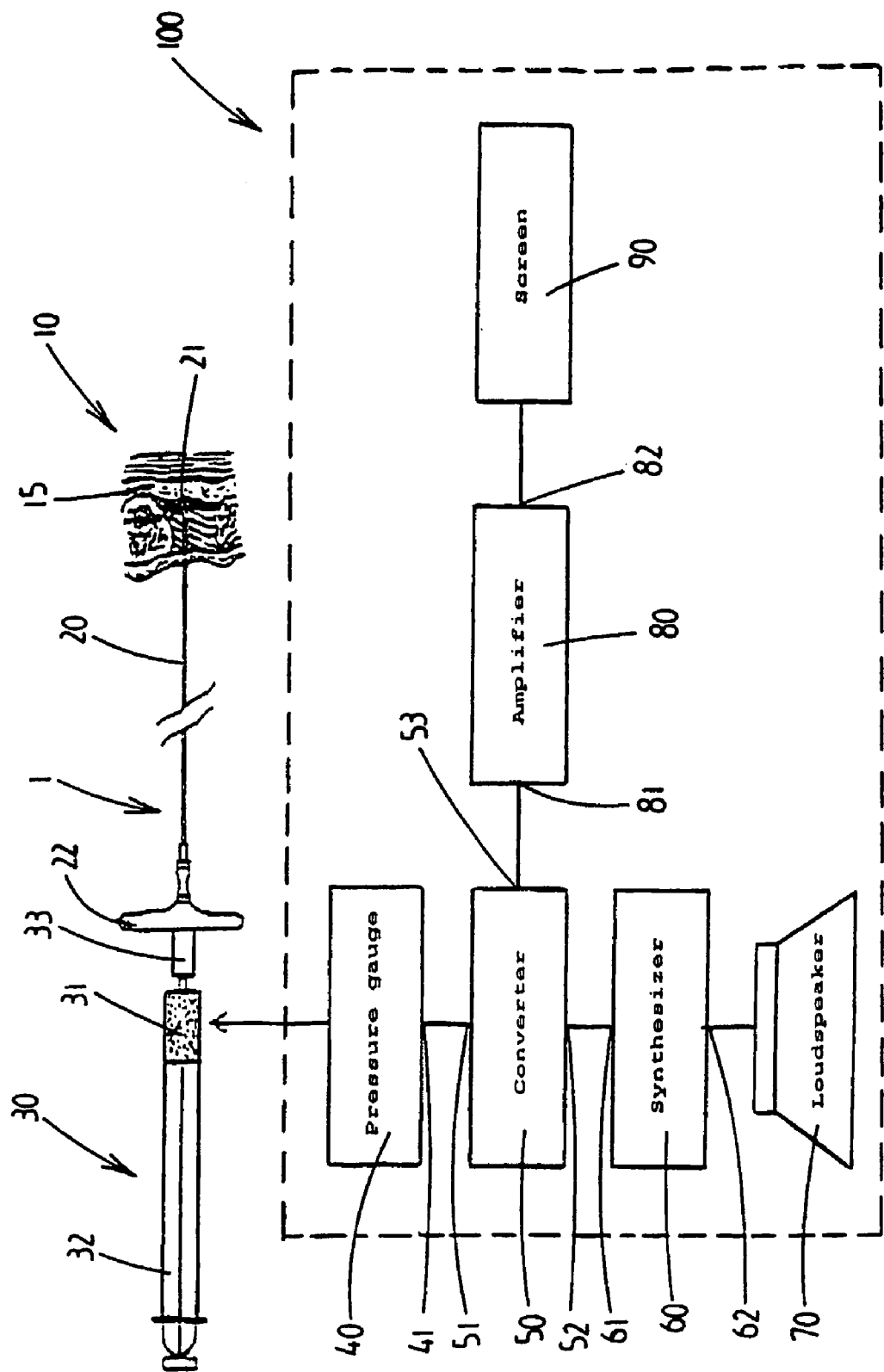
FIG. 1 shows a side view of a first preferred embodiment of the device according to the invention, in which a section of the device is illustrated diagrammatically, and FIG. 2 diagrammatically depicts a section of a second preferred embodiment of the device according to the invention.

FIG. 1 shows a first preferred embodiment of the device according to the invention, which is denoted overall by reference numeral 1.

FIG. 1 shows one of the possible uses of the device 1, specifically its use for locating an anatomical cavity, in particular the epidural cavity, in a human body. A small section of a human body is illustrated in cross section in FIG. 1 and is denoted by reference numeral 10. The anatomical cavity or epidural cavity is denoted by reference numeral 15.

The device 1 comprises a hollow puncture needle 20 with a needle point 21. In the example shown in FIG. 1, the puncture needle 20 has been introduced part way into the body 10 and the needle point 21 is situated in the vicinity of the epidural cavity 15. The puncture needle 20 is provided with a handle 22, which can be held by the person who is handling the puncture needle 20, for example a physician. This handle 22 enables the user to exert a pushing or pulling force on the puncture needle 20, in order for it to be moved in a desired direction.

A reservoir 30 in the form of an injection syringe is positioned in line with the puncture needle 20. The reservoir 30 comprises a fluid-filled space 31 and a displaceable plunger 32 which closes off the said reservoir 30 in a sealed manner on one side. The displaceable plunger 32 in this case functions as a pump means for generating pressure in the fluid in the reservoir 30. As an alternative to using a plunger as the pump means, it is also possible, for example, to use bellows or other suitable pump means. The reservoir 30 is in communication with the puncture needle 20 via a connection part 33, it being possible for fluid to flow out of the said reservoir 30 into the said puncture needle 20. The fluid in the reservoir 30 may be a gas or a liquid, for example a sterile, isotonic liquid. In the text which follows, the invention is discussed on the basis of the example according to which an isotonic liquid is situated in the reservoir 30, but the invention can equally well be applied to an embodiment in which a gas is situated in the reservoir 30.

To measure the pressure in the liquid in the reservoir 30, the locating device 1 is provided with an electrical pressure gauge 40. An output 41 of the pressure gauge 40 is connected to an input 51 of a signal converter 50, which is able to convert a pressure-measurement signal provided by the pressure gauge 40 into a form which can be used for further processing, for example an electric voltage. The signal converter 50 is designed to emit the converted pressure-measurement signal both at an acoustic output 52 and at a visual output 53. It should be noted that the pressure gauge 40 and the signal converter 50 can form a single unit instead of two separate elements.

One input 61 of a synthesizer 60 is connected to the acoustic output 52. The synthesizer 60 is designed to process the converted pressure-measurement signal to form a sound signal which is representative of the pressure prevailing in the reservoir 30 and therefore of the said converted pressure-measurement signal. The synthesizer 60 is connected via an output 62 to a loudspeaker 70 for emitting the sound signal. If appropriate, an audio amplifier (not shown in more detail) is also provided, for the purpose of amplifying the sound signal.

On account of the relationship between the sound signal and the converted pressure-measurement signal, the sound signal is representative of the pressure which is prevailing in the liquid in the reservoir 30. One or more aspects of the sound signal may be directly and continuously related to the converted pressure-measurement signal, depending on the setting of synthesizer 60. For example, the pitch of the sound signal may be representative of the pressure, but it is also possible, for example, that the volume or the pulse frequency, if the sound signal has a pulsating character, may be representative of the pressure. Another possibility is for a suitable combination of the pitch, the volume and the pulse frequency to be used. One possible combination which may be suitable is, for example, the use of the pitch as a measure of the pressure and the volume as a measure of the rate at which the pressure is changing, in which case, by way of example, in the event of a rapid pressure change a stronger sound signal is emitted than in the event of a slow change. In this example, another possibility is to swap the pitch and volume.

An input 81 of an amplifier 80 is connected to the visual output 53 and is designed to emit an amplified, converted pressure-measurement signal at an output 82. The amplifier 80 is connected via the output 82 to a screen 90 for displaying a visual signal which is representative of the pressure in the liquid in the reservoir 30 on the basis of the amplified, converted pressure-measurement signal.

The assembly comprising pressure gauge 40, signal converter 50, synthesizer 60, loudspeaker 70, amplifier 80 and screen 90 is referred to below as the measuring and reproduction unit 100, as shown by a dashed line in FIG. 1.

Before the device 1 can be used to locate the epidural cavity 15 in the body 10, the puncture needle 20 can first of all be introduced a small depth into the body 10 in the vicinity of where the epidural cavity is situated. Then, the reservoir 30 and the measuring and reproduction unit 100 coupled thereto can be connected to the puncture needle 20. It is also possible for all the components to be connected to one another first of all and then for the liquid to be pressurized, and for the puncture needle 21 to be introduced into the body 10 as soon as the liquid emerges from the needle 20. The latter method is preferred, since in this case the measurement of the pressure can commence immediately.

If the person who is handling the device 1 exerts force on the plunger 32, pressure will be built up in the liquid which is situated in the reservoir 30. As a result of this pressure, the liquid will tend to flow out of the unit comprising reservoir 30 and puncture needle 20 via the needle point 21. In the process, the liquid which emerges at the needle point 21 is subject to a resistance to absorption of the liquid by the tissue in which the needle point 21 is situated. This resistance is expressed as a pressure which has to be overcome by the person who is handling the device 1 by exerting a force on the plunger 32. If the person who is handling the device 1 always ensures a (slight) displacement of the plunger 32 while he is moving the puncture needle 20 towards the epidural cavity 15, the force exerted on the plunger 32, and therefore the pressure prevailing in the liquid, is always a measure of the pressure at the needle point 21.

The synthesizer 60 is set in such a manner that the sound signal which is emitted is representative of the measured pressure, with the result that the sound signal is always an acoustic reproduction of the instantaneous pressure in the liquid.

Any changes in the resistance which the liquid experiences as it leaves the needle point 21 have a direct influence on the pressure in the reservoir 30. The changes in the pressure in the reservoir 30 in turn directly lead to changes in the sound signal. The person who is handling the puncture needle 20 can therefore use any changes in the sound signal which he detects over the course of time to determine what changes are occurring in the pressure. If the possibility of a visual reproduction is being used, the same-applies to the visual signal.

When the epidural cavity 15 has been reached by the needle point 21, the liquid which emerges will be subject to considerably less resistance. As a result, less force has to be exerted on the plunger 32 in order to displace the liquid out of the reservoir 30. As a result, the pressure in the reservoir 30 will drop. With this knowledge, it can be inferred from a sudden and significant change in the sound signal that the needle point 21 has reached the epidural cavity 15 and that movement of the puncture needle 20 into the body 10 can be stopped. If the possibility of a visual reproduction is being-used, the person who is handling the device 1 can look at the screen 90 and see confirmation that the epidural cavity 15 has been reached.

When using the device 1, calibration of the pressure-measurement signal is not critical, since the user is working on the basis of changes which he detects in the sound signal; the absolute value of, for example, the volume or pitch of the sound signal is of subordinate importance.

The continuous pressure-measurement signal is likewise fed by the signal converter 50, as a voltage signal, via the visual output 53 to the input 81 of the amplifier 80. Via the output 82, the pressure-measurement signal is supplied in amplified form to the screen 90, which emits a visual signal on the basis of the pressure-measurement signal which is supplied. In this case too, there is a relationship between the pressure-measurement signal and the visual signal, the visual signal being representative of the pressure at the needle point 21.

The screen 90 may, for example, be designed to reproduce the visual signal in the form of numerical values or plotted in the form of a curve of the measured pressure against time. The visual reproduction in the form of a curve of the pressure plotted against time is particularly preferred, since it has been found that reaching the epidural cavity 15 results in a highly characteristic and therefore highly recognisable curve. The screen 90 may be provided with means which allow the numerical values to be calibrated, but this is not imperative, since the user can, in the case of the visual signal as well, work on the basis of changes in said signal to determine whether or not the needle point 21 has reached the epidural cavity 15.

During the introduction of the needle 20 into the body, the continuous sound signal is of greater importance than the continuous visual signal. This is because the user cannot continuously look at the screen 90 in order to observe the visual signal, since he must also at least look at the puncture needle 20 during the movement thereof. To handle the device 1, the user can in principle rely entirely on the sound signal and use his eyes to look at the movement of the puncture needle 20.

The sound signal can provide the user with sufficient information with regard to the pressure at the needle point 21. Therefore, in the device 1 according to the invention, the visual output 53 on the signal converter 50, the amplifier 80 and the screen 90 can be omitted if desired, and therefore the device 1 according to the invention provided with the visual output 53 at the signal converter 50, the amplifier 80 and the screen 90 forms a particular variant of the first preferred embodiment. However, as has been mentioned, the visual signal does offer a monitoring option.

Figure 2:
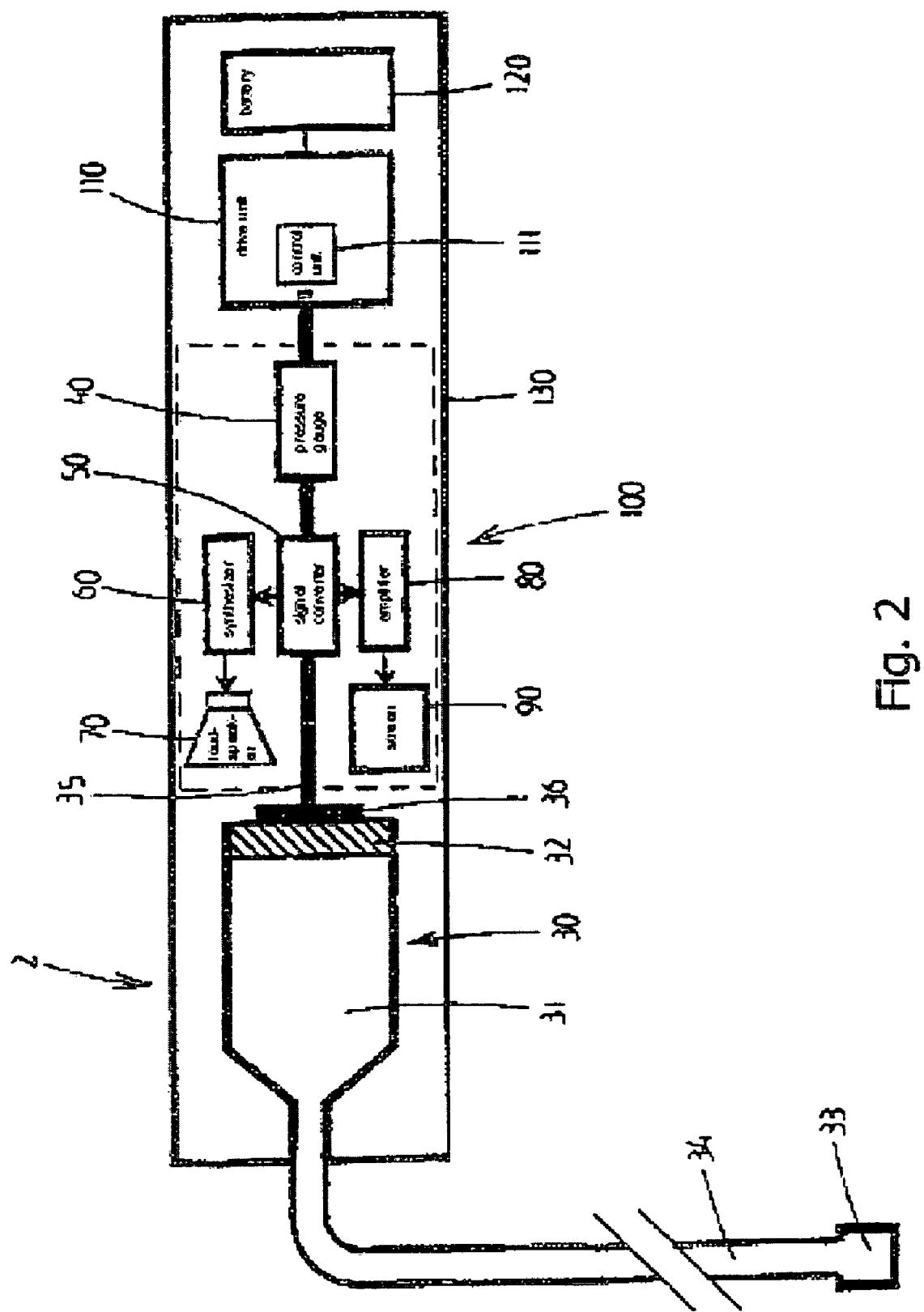

FIG. 2 diagrammatically depicts a section of a second preferred embodiment of a device 2 according to the invention. The second embodiment of the device 2 comprises the same components as the first preferred embodiment shown in FIG. 1.

The hollow puncture needle 20 (cf. FIG. 1) which forms part of the device 2 is not shown in FIG. 2. The reservoir 30 is connected to the puncture needle by means of a hose 34 and the connection part 33.

The device 2 is provided with automatic pump means which are designed to displace the fluid, and in particular the plunger 32 and the liquid situated beneath it (or if desired a gas mixture) in the reservoir 31 as a result of a force being exerted on the plunger 32. For this purpose, the device 2 comprises a connecting rod 35, one end of which is connected to a drive unit 110 and the other end of which is provided with a pressure disc 36. The drive unit 110 is used to exert a force on the connecting rod 35 in order to effect a movement in the axial direction of the connecting rod 35. The pressure disc 36 is intended to bear against at least part of the surface of the plunger 32. By way of example, the drive unit 110 may be an electric motor which is connected to a (storage) battery 120. An example of a suitable drive unit for the preferably automatic displacement of the plunger 32 is an injection pump which is known in the specialist field. A pump of this type is particularly suitable for delivering small quantities of liquid with a high degree of accuracy. Other possibilities are conceivable for supplying energy to the drive unit 110. For example, the device 2 could be provided with means for connecting the drive unit 110 to the mains. It is also possible to arrange a pump between the reservoir 30 and the needle 20. In this case, the pump means do not generate any pressure in the reservoir, but rather suck the liquid out of the reservoir and pump it through the needle under pressure. Therefore, the measurement of the pressure in the reservoir as described above can no longer take place, but rather will have to take place either in the needle or immediately after the pump. Another possibility for determining the pressure generated is that of measuring the power consumed by the pump means and using this information to calculate the pressure difference which has been generated by the pump means. This possibility is not shown in more detail.

A significant advantage of the automatic displacement of the plunger 32 is that the person who is using the device 2 can use both hands to move the puncture needle. As has already been stated in the description of the first preferred embodiment of the device (FIG. 1), the pressure in the reservoir 30 is continuously rendered audible by means of an acoustic signal. Consequently, it is not necessary for the person who is handling the device to exert pressure on the plunger 32 himself. However, this is required, for example, when the device which is known from EP 0 538 259 is being used.

The reservoir 30, the connecting rod 35, the drive unit 110 and the (storage) battery 120 are all arranged in the interior of a housing 130, as is the measuring and reproduction unit 100, which is diagrammatically indicated by a dashed line in FIG. 2. An arrangement of this type is preferred, since it results in a compact assembly which can easily be connected to the puncture needle.

The reservoir 30 is accommodated in a space which is created for this purpose in the housing 130, which at the location of the said space is preferably designed in such a manner that a reservoir 30 can easily be placed into the housing 130 before use and can easily be removed again from the housing 130 after use.

Clamping means (not shown) may be provided on the exterior of the housing 130, in order to allow the said housing 130 to be clamped to any desired object, such as for example a table or a bed.

In this example, the pressure gauge 40 comprises a force pick-up which is designed to pick up the force exerted on the connecting rod 35 by the drive unit 110. In this case, the signal converter 50 is designed as a force-voltage converter. The drive unit 110 comprises a control unit 111 which is connected to the force pick-up of the pressure gauge 40. The control device 111 is responsible for displacement of the plunger 32 at a continuous rate and therefore for producing a constant mass flow of the liquid through the needle. As a result of the displacement of the plunger 32, pressure will be built up in the liquid which is situated in the reservoir 30. As a result of this pressure, the liquid will tend to flow out of the assembly comprising reservoir 30 and puncture needle via the needle point. In the process, the liquid which emerges at the needle point is subject to a resistance to absorption of the liquid by the tissue in which the needle point is situated. This resistance manifests itself as a pressure which has to be overcome by the drive unit 110 as a result of a force being exerted on the plunger 32. The continuous but slow rate at which the plunger 32 is being displaced while the puncture needle is being moved in the direction of the epidural cavity means that the force exerted on the plunger 32, and therefore the pressure prevailing in the liquid, will always be a measure of the pressure at the needle point.

Although it is preferred for the plunger 32 to be moved at a constant rate, it is also possible for the plunger 32 to be moved in steps. In this case, however, it is preferable for the movement steps to follow one another at sufficiently short intervals for the risk of the needle being introduced too far to be avoided.

The force with which the drive unit 110 presses on the plunger 32 is controlled by the control device 111. For safety reasons, the control device 111 may be provided with a pressure limiter, which limits the maximum pressure prevailing in the liquid and therefore the maximum force which can be exerted on the plunger 32. This prevents the possibility of force being exerted on the plunger 32 in an uncontrolled manner and ultimately of the body being damaged if liquid is forced into the body with considerable force.

For suitable driving, a section of the connecting rod 35 may be provided with helical toothing, in which case the drive unit 110 is provided with a driven toothed wheel which meshes with the said section. The force pick-up of the pressure gauge 40 may in this case be designed to measure the force exerted on the connecting rod 35 by the wheel.

The process of locating the epidural cavity begins with pressurizing an isotonic liquid, for example, in the reservoir 30 by means of a displacement of the plunger 32 in the direction of the hose 34. For this purpose, the drive unit 110 exerts a force, which is directed to the left in FIG. 2, on the connecting rod 35. As a result of this force, the connecting rod 35 will move in the axial direction and the plunger 32 will likewise move in the direction of the hose 34, via the pressure disc 36. In the process, the liquid tends to move towards the body and in the process is subject, as has already been discussed, to a resistance from the tissue of the body, which is experienced as a counterpressure which is exerted by the body and is translated into a pressure in the liquid.

The force which is exerted on the connecting rod 35 by the drive unit 110 in order to inject the liquid into the tissue of the body is directly related to the pressure at the needle point and must overcome at least the said resistance. If the needle point is moving through substantially homogeneous tissue, the pressure at the needle point scarcely changes and the force which is to be exerted is virtually constant. The amplifier 70 will in this case emit a sound signal which likewise scarcely changes.

The drive unit 110 is designed to move the connecting rod 35 at a constant, preferably low rate after the liquid in the reservoir 30 has been brought to the said starting pressure. As the tissue will not always present the same resistance to absorption of the liquid, the force with which the drive unit 110 presses on the plunger 32 will change when the needle point is then being moved through the tissue of the body, since a constant movement/movement rate of the plunger 32 is desired. As a result, the pressure in the liquid will likewise change during the movement of the needle point. The measuring and reproduction unit 100, as has been described with reference to FIG. 1, measures the pressure and supplies an acoustic and/or visual signal.

When the needle point reaches the epidural cavity, the liquid flows into the epidural cavity and the resistance to absorption of the liquid will drop suddenly and significantly. As a result, the pressure prevailing in the liquid will likewise drop suddenly and significantly. At that time, the drive unit 110 has to exert in relative terms a much lower force in order to move the connecting rod 35 than was the case before the epidural cavity was reached. The sudden and significant change in the force is observed by the person who is handling the device 2 as a sudden and significant change in the sound signal and also, if appropriate, in the visual signal. The person who is handling the device 2 can infer from a change of this type that the needle point has reached the epidural cavity and that he must stop moving the puncture needle. He can then disconnect the connection between the puncture needle and the remaining components of the device at the connection part 33, in order for an injection syringe containing the substances which are to be introduced into the epidural cavity to be placed on to the puncture needle or in order to introduce what is known as an epidural catheter.

In an embodiment which is not shown in more detail, the device according to the invention comprises recording means for recording the profile of the pressure-measurement signal over the course of time. In particular, consideration may be given to an electronic memory in which the measured pressure data are stored and can subsequently be retrieved, or, for example, a magnetizable storage means. However, it is also possible for the profile of the pressure-measurement signal to be printed directly onto paper.

A major advantage of recording means of this type is that it is possible to retrospectively assess whether, and if necessary to demonstrate that, the person who is handling the device did in fact reach the intended anatomical cavity. This advantage is all the greater if the recorded pressure data are stored during the movement of the needle in the body in such a way that, with this data, it is easy to produce a curve in which the measured pressure is plotted against time. As has already been noted above, a visual reproduction in the form of a curve of the pressure plotted against time is highly advantageous, since reaching the anatomical cavity produces a very characteristic and therefore very recognisable curve. It should be noted that recording means for storing pressure-measurement data may also be used separately of the inventive idea. The recording means do not necessarily have to be used in combination with reproduction means for generating an acoustic or visual signal. The storage is important for subsequent reference to the pressure-measurement data.

The scope of the present invention is not restricted to the examples which have been discussed above, but rather various changes and modifications to these examples are possible without departing from the scope of the invention as defined in the appended claims.

For example, it is also possible for the inventive idea to be applied to a step which often follows the step of locating an epidural cavity, namely the positioning of an epidural catheter in the epidural cavity.

The locating of the epidural cavity is often a preparatory step to administering an anaesthetizing substance via the said catheter. In this case, it is important for the end of the catheter to be located at the correct location, i.e. in the epidural cavity.

The catheter can be introduced by disconnecting the reservoir from the puncture needle after the needle point has reached the epidural cavity and then guiding the catheter via the puncture needle into the epidural cavity. Often, the person who is positioning the catheter will have a reasonable feeling of when the catheter has been correctly positioned, but more certainty with regard to correct positioning is desirable. The measuring and signalling device according to the present invention can advantageously be used in this context.

When the catheter has been introduced via the puncture needle, its correct positioning can be checked by pressurizing the liquid which is to be introduced and measuring the pressure, and in particular the change(s) in this pressure, using the measuring and signalling device according to any desired preferred embodiment of the measuring and signalling device.

While the liquid in the catheter is being pressurized, which is the result of the liquid being fed to the catheter, the pressure of the liquid will initially increase. If the liquid is then pumped through the catheter and if the end of the catheter is in fact located in the epidural cavity, the liquid will be able to flow virtually unimpeded into the epidural cavity, the pressure in the liquid will therefore not change or will scarcely change, and there will be virtually no change in the acoustic signal and/or the visual signal which is generated by the measuring and signalling device. The person who is carrying out the operation will immediately know that the catheter has been positioned correctly and will be able to fix the catheter in place.

The above text has described an application of the device according to the invention for locating an epidural cavity in a human body. This does not detract from the fact that the device can also be used to locate a region which is situated in a body and in terms of its properties differs from the area which immediately surrounds it. In this context, consideration may be given, for example, to locating an intumescence or a tumour in the body of a person. A tumour generally has different properties from the surrounding tissue in which it is situated, and in particular the tumour will present a different resistance to the penetration of a fluid compared to the surrounding tissue. If the device according to the invention is used in a similar way to that described above, a sudden change in the measured pressure at the needle point will indicate that the area which is being looked for has been reached. In this context, it is assumed that pressure variations which occur in the fluid during displacement of the needle in a section of the body which precedes the area which is to be located are much smaller than the pressure variation which occurs in the fluid when the needle point reaches the said area. It is advantageous if it is known how the area which is to be located differs from the part which surrounds this area, so that it is possible to establish with a high degree of certainty that the area which is to be located has in fact been found.

The device can also be used to locate any desired cavity in any desired body, once again assuming that pressure variations which occur in the fluid during displacement of the puncture needle in a section of the body which precedes the cavity are significantly smaller than the pressure variation which occurs in the fluid when the needle point reaches the cavity.

Furthermore, the above text has described the device according to the invention using an isotonic liquid. As has already been noted above, it is also possible to use a gas. However, a gas is a medium which can be compressed to a much greater extent than a liquid. To compensate for this while the device is being used and to ensure a constant mass flow of the gas during use of the device, the device may be provided with additional control means.

What is claimed is:

1. Assembly for a device for locating a region which is situated in a body, comprising:
   a hollow needle for locating the region;
   a fluid-filled reservoir which is in communication with said needle; and
   a pump for pressurizing the fluid;
   a measuring device for creating a pressure-measurement signal which is related to pressure prevailing in the fluid-filled reservoir;
   a signal-converter designed for converting said pressure-measurement signal created by said measuring device into a converted signal which is suitable for further processing; and
   a reproduction device designed for processing the converted signal to emit an acoustic signal which is related to the converted signal;
   wherein said converted signal and said acoustic signal are both continuously representative of the instantaneous pressure prevailing in the fluid in order to provide that the acoustic signal is always an acoustic reproduction of the instantaneous pressure prevailing in the fluid such that changes in said pressure directly lead to changes in the acoustic signal.

2. Assembly according to claim 1, wherein said reproduction device emits an acoustic signal having a volume that is continuously representative of the instantaneous pressure prevailing in the fluid.

3. Assembly according to claim 1, wherein said signal-converter is designed to emit said pressure-measurement signal in the form of an electric voltage.

4. Assembly according to claim 1, wherein said reproduction device comprises a synthesizer, an audio amplifier and a loudspeaker.

5. Assembly according to claim 1, wherein said reproduction device comprises a visual reproduction device for continuously emitting a visual signal which is continuously representative of the instantaneous pressure prevailing in the fluid.

6. Assembly according to claim 5, wherein the visual reproduction device comprises an amplifier and a screen.

7. Assembly according to claim 1, comprising a recorder for recording the profile of said pressure-measurement signal over the course of time.

8. Assembly according to claim 1, wherein said pump comprises a displaceable plunger.

9. Assembly according to claim 8, wherein said pump comprises an automatic pump for automatically pumping fluid.

10. Assembly according to claim 9, wherein said automatic pump is designed to continuously deliver fluid.

11. Assembly according to claim 9, wherein said pump comprises a drive unit which is designed to displace said plunger in said reservoir.

12. Assembly according to claim 11, wherein said measuring device is designed to pick up the force which is exerted on said plunger by said drive unit.

13. Assembly according to claim 11, wherein said pump is provided with a displaceable connecting rod, one end of which is intended to bear against said displaceable plunger, and with a drive unit for effecting a displacement of said connecting rod.

14. Assembly according to claim 13, wherein said measuring device is provided with a force pick-up for picking up the force exerted on said connecting rod.

15. Assembly according to claim 14, wherein said signal-converter comprises a force-voltage converter.

16. Assembly according to claim 13, wherein at least a section of said connecting rod is provided with helical toothing.

17. Assembly according to claim 1, comprising a pressure-limiting device for limiting fluid pressure.

18. The assembly according to claim 1, further comprising:
   a housing that defines a space which is located in the interior of said housing and is suitable for accommodating the fluid-filled reservoir which is connected to said pump;
wherein said assembly is capable of locating a region which is situated in a body.

19. Assembly according to claim 18, comprising a clamp for clamping said device to any desired object, said clamp disposed on the exterior of said housing.

* * * * *